(12) United States Patent
Pfeiffer et al.

(10) Patent No.: US 8,770,282 B2
(45) Date of Patent: Jul. 8, 2014

(54) CHEMICAL AMENDMENTS FOR THE STIMULATION OF BIOGENIC GAS GENERATION IN DEPOSITS OF CARBONACEOUS MATERIAL

(75) Inventors: Robert S. Pfeiffer, Parker, CO (US); Glenn A. Ulrich, Golden, CO (US)

(73) Assignee: Transworld Technologies Inc., Houston, TX (US)

( * ) Notice: Subject to any disclaimer, the term of this patent is extended or adjusted under 35 U.S.C. 154(b) by 183 days.

(21) Appl. No.: 12/751,745

(22) Filed: Mar. 31, 2010

(65) Prior Publication Data

US 2010/0190203 A1  Jul. 29, 2010

Related U.S. Application Data

(62) Division of application No. 11/399,099, filed on Apr. 5, 2006, now Pat. No. 7,696,132.

(51) Int. Cl.
*C09K 8/60* (2006.01)
*E21B 43/22* (2006.01)
*C12P 5/02* (2006.01)
*C10G 32/00* (2006.01)
*C12N 1/00* (2006.01)

(52) U.S. Cl.
USPC ............. 166/246; 166/401; 435/41; 435/167; 435/281; 507/201

(58) Field of Classification Search
USPC ............. 166/246, 401; 507/201; 435/41, 167, 435/281
See application file for complete search history.

(56) References Cited

U.S. PATENT DOCUMENTS

| | | |
|---|---|---|
| 1,990,523 A | 2/1935 | Buswell et al. |
| 2,413,278 A | 12/1946 | Zobell |
| 2,641,566 A | 6/1953 | Zobell |
| 2,659,659 A | 11/1953 | Schmidl |
| 2,660,550 A | 11/1953 | Updegraff et al. |
| 2,807,570 A | 9/1957 | Updegraff |
| 2,907,389 A | 10/1959 | Hitzman |
| 2,975,835 A | 3/1961 | Bond |
| 3,006,755 A | 10/1961 | Adams |
| 2,185,216 A | 5/1965 | Hitzman |
| 3,185,216 A | 5/1965 | Hitzman |
| 3,332,487 A | 7/1967 | Jones |
| 3,340,930 A | 9/1967 | Hitzman |
| 3,437,654 A | 4/1969 | Dix |
| 3,637,686 A | 1/1972 | Kokubo et al. |
| 3,640,846 A | 2/1972 | Johnson |
| 3,724,542 A | 4/1973 | Hamilton |
| 3,800,872 A | 4/1974 | Friedman |
| 3,826,308 A | 7/1974 | Compere-Whitney |
| 3,982,995 A | 9/1976 | Yen et al. |
| 4,184,547 A | 1/1980 | Klass et al. |
| 4,300,632 A | 11/1981 | Wiberger et al. |
| 4,316,961 A | 2/1982 | Klass et al. |
| 4,329,428 A | 5/1982 | Ghosh et al. |
| 4,349,633 A | 9/1982 | Worne et al. |
| 4,358,535 A | 11/1982 | Falkow et al. |
| 4,358,537 A | 11/1982 | Chynoweth |
| 4,386,159 A | 5/1983 | Kanai |
| RE31,347 E | 8/1983 | Reijonen et al. |
| 4,416,332 A | 11/1983 | Wiberger et al. |
| 4,424,064 A | 1/1984 | Klass et al. |
| 4,446,919 A | 5/1984 | Hitzman |
| 4,450,908 A | 5/1984 | Hitzman |
| 4,475,590 A | 10/1984 | Brown |
| 4,481,293 A | 11/1984 | Thomsen et al. |
| 4,522,261 A | 6/1985 | McInerney et al. |
| 4,562,156 A | 12/1985 | Isbister et al. |
| 4,579,562 A | 4/1986 | Tarman et al. |
| 4,610,302 A | 9/1986 | Clark |
| 4,640,767 A | 2/1987 | Zajic et al. |
| 4,666,605 A | 5/1987 | Minami et al. |
| 4,678,033 A | 7/1987 | Killough |
| 4,743,383 A | 5/1988 | Stewart et al. |
| 4,799,545 A | 1/1989 | Silver et al. |
| 4,826,769 A | 5/1989 | Menger |
| 4,845,034 A | 7/1989 | Menger et al. |

(Continued)

FOREIGN PATENT DOCUMENTS

| | | |
|---|---|---|
| DE | 4036787 B1 | 5/1992 |
| DE | 4115435 B2 | 8/1992 |

(Continued)

OTHER PUBLICATIONS

EP Supplemental Search Report mailed Nov. 5, 2010; Application No. 08771271.7, 6 pages.

(Continued)

*Primary Examiner* — Taeyoon Kim
(74) *Attorney, Agent, or Firm* — Kilpatrick Townsend & Stockton LLP

(57) ABSTRACT

Methods of stimulating biogenic production of a metabolic product with enhanced hydrogen content are described. The methods may include accessing a consortium of microorganisms in a geologic formation that includes a carbonaceous material. They may also include providing hydrogen and one or more phosphorous compounds to the microorganisms. The combination of the hydrogen and phosphorous compounds stimulates the consortium to metabolize the carbonaceous material into the metabolic product with enhanced hydrogen content. Also, methods of stimulating biogenic production of a metabolic product with enhanced hydrogen content by providing a carboxylate compound, such as acetate, to a consortium of microorganisms is described. The carboxylate compound stimulates the consortium to metabolize carbonaceous material in the formation into the metabolic product with enhanced hydrogen content.

20 Claims, 7 Drawing Sheets

(56) References Cited

U.S. PATENT DOCUMENTS

| | | |
|---|---|---|
| 4,883,753 A | 11/1989 | Belaich et al. |
| 4,905,761 A | 3/1990 | Bryant |
| 4,906,575 A | 3/1990 | Silver et al. |
| 4,914,024 A | 4/1990 | Strandberg et al. |
| 4,947,932 A | 8/1990 | Silver et al. |
| 4,969,130 A | 11/1990 | Wason et al. |
| 4,971,151 A | 11/1990 | Sheehy |
| 5,044,435 A | 9/1991 | Sperl et al. |
| 5,076,927 A | 12/1991 | Hunter |
| 5,081,023 A | 1/1992 | Yaginuma et al. |
| 5,083,610 A | 1/1992 | Sheehy |
| 5,083,611 A | 1/1992 | Clark et al. |
| 5,087,558 A | 2/1992 | Webster, Jr. |
| 5,100,553 A | 3/1992 | Nomura et al. |
| 5,155,042 A | 10/1992 | Lupton et al. |
| 5,163,510 A | 11/1992 | Sunde |
| 5,250,427 A | 10/1993 | Weaver et al. |
| 5,297,625 A | 3/1994 | Premuzic et al. |
| 5,327,967 A | 7/1994 | Jenneman et al. |
| 5,340,376 A | 8/1994 | Cunningham |
| 5,341,875 A | 8/1994 | Jenneman et al. |
| 5,350,684 A | 9/1994 | Nakatsugawa et al. |
| 5,360,064 A | 11/1994 | Jenneman et al. |
| 5,363,913 A | 11/1994 | Jenneman et al. |
| 5,368,099 A | 11/1994 | Davey et al. |
| 5,424,195 A | 6/1995 | Volkwein |
| 5,490,634 A | 2/1996 | Jain et al. |
| 5,492,828 A | 2/1996 | Premuzic et al. |
| 5,500,123 A | 3/1996 | Srivastava |
| 5,510,033 A | 4/1996 | Ensley et al. |
| 5,516,971 A | 5/1996 | Hurley |
| 5,538,530 A | 7/1996 | Heaton et al. |
| 5,551,515 A | 9/1996 | Fodge et al. |
| 5,560,737 A | 10/1996 | Schuring et al. |
| 5,593,886 A | 1/1997 | Gaddy |
| 5,593,888 A | 1/1997 | Glaze et al. |
| 5,597,730 A | 1/1997 | Aust et al. |
| 5,630,942 A | 5/1997 | Steiner |
| 5,670,345 A | 9/1997 | Srivastava et al. |
| 5,695,641 A | 12/1997 | Cosulich et al. |
| 5,723,597 A | 3/1998 | Kohne |
| 5,763,736 A | 6/1998 | Daume |
| 5,766,929 A | 6/1998 | Orolin et al. |
| 5,783,081 A | 7/1998 | Gaddy |
| 5,821,111 A | 10/1998 | Grady et al. |
| 5,854,032 A | 12/1998 | Srivastava et al. |
| 5,858,766 A | 1/1999 | Premuzic et al. |
| 5,885,825 A | 3/1999 | Lin et al. |
| 5,919,696 A | 7/1999 | Ikeda et al. |
| 5,928,864 A | 7/1999 | Kohne |
| 5,955,261 A | 9/1999 | Kohne |
| 5,955,262 A | 9/1999 | Kourilsky et al. |
| 6,090,593 A | 7/2000 | Fleming et al. |
| 6,143,534 A | 11/2000 | Menger et al. |
| 6,202,051 B1 | 3/2001 | Woolston |
| 6,210,955 B1 | 4/2001 | Hayes |
| 6,265,205 B1 | 7/2001 | Hitchens et al. |
| 6,340,581 B1 | 1/2002 | Gaddy |
| 6,348,639 B1 | 2/2002 | Crawford et al. |
| 6,420,594 B1* | 7/2002 | Farone et al. ............ 560/185 |
| 6,543,535 B2 | 4/2003 | Converse et al. |
| 6,758,270 B1 | 7/2004 | Sunde et al. |
| 6,795,922 B2 | 9/2004 | Johnson et al. |
| 6,859,880 B2 | 2/2005 | Johnson et al. |
| 7,696,132 B2 | 4/2010 | Pfeiffer et al. |
| 7,977,282 B2 | 7/2011 | Pfeiffer et al. |
| 8,092,559 B2 | 1/2012 | Debryun et al. |
| 2001/0045279 A1 | 11/2001 | Converse et al. |
| 2003/0062270 A1 | 4/2003 | McAlister |
| 2003/0205458 A1 | 11/2003 | Roychowdhury |
| 2003/0216353 A1 | 11/2003 | Mosher et al. |
| 2003/0232423 A1* | 12/2003 | Priester et al. ............ 435/262 |
| 2004/0033557 A1 | 2/2004 | Scott et al. |
| 2004/0035785 A1 | 2/2004 | Rebholz |
| 2004/0228833 A1 | 11/2004 | Costantino et al. |
| 2005/0053955 A1 | 3/2005 | Sowlay et al. |
| 2005/0269261 A1 | 12/2005 | Sublette |
| 2006/0223153 A1 | 10/2006 | Pfeiffer |
| 2006/0223159 A1 | 10/2006 | Pfeiffer |
| 2006/0223160 A1 | 10/2006 | Vanzin |
| 2006/0237097 A1 | 10/2006 | Lau et al. |
| 2006/0254765 A1 | 11/2006 | Pfeiffer et al. |
| 2007/0151729 A1 | 7/2007 | Hoch et al. |
| 2007/0248531 A1 | 10/2007 | Debryun et al. |
| 2007/0295505 A1 | 12/2007 | Pfeiffer et al. |
| 2008/0299635 A1 | 12/2008 | Pfeiffer et al. |
| 2010/0248321 A1 | 9/2010 | Steaffens et al. |
| 2010/0248322 A1 | 9/2010 | Pfeiffer et al. |

FOREIGN PATENT DOCUMENTS

| | | |
|---|---|---|
| DE | 19520548 B3 | 12/1996 |
| JP | 09 121868 B4 | 5/1997 |
| WO | WO 79/00201 B5 | 4/1979 |
| WO | WO 89/10463 A1 | 11/1989 |
| WO | WO 92/13172 A1 | 8/1992 |
| WO | WO 01/68904 B6 | 9/2001 |
| WO | WO 02/06503 A | 1/2002 |
| WO | WO 02/34931 A2 | 5/2002 |
| WO | WO 2004/071195 A1 | 8/2004 |
| WO | WO 2005/115648 A1 | 12/2005 |
| WO | WO 2007/022122 A1 | 2/2007 |
| WO | WO 2007/118094 A2 | 10/2007 |

OTHER PUBLICATIONS

Aitken, Carolyn M. et al "Anaerobic hydrocarbon degradation in deep subsurface oil reserves" Nature, Sep. 16, 2004, pp. 291-294.

Anderson, Robert T., and Lovley, Derek R., "Hexadecane Decay by Methanogenesis", Nature, v. 404, p. 722, Apr. 13, 2000.

Anderson, Robert T., Rooney-Varga, Juliette N., et al., "Anaerobic Benzene Oxidation in the Fe(III) Reduction Zone of Petroleum-Contaminated Aquifers", Environmental Science & Technology, v. 32, pp. 1222-1229, 1998.

Artech Inc., Biological Gasification of Coals. Final Report, U.S. Department of Energy, Contract DE-AC21-87MC23285, pp. 40-63, 1990.

Basiliko, Nathan et al. "Influence of Ni, Co, Fe, and Na additions on methane production in Sphagnum dominated Northern American peatlands" Biogeochemistry, 2001, 52: 133-153.

Belyaev, S. S., et al. "Methanogenic Bacteria from the Bondyuzhskoe Oil Field: General Characterization and Analysis of Stable-Carbon Isotopic Fractionation" Applied and Environmental Microbiology, 1983, v. 45, No. 2, pp. 691-697.

Bernard, F. P., et al. "Indigenous Microorganisms in Connate Water of Many Oil Fields: A New Tool in Exploration and Production Techniques" SPE 24811, 1992, pp. 467-476.

Biville, F. et al., "In vivo positive effects of exogenous pyrophosphate on *Escherichia coli* cell growth and stationary phase survival", Res. Microbiol. 1996, 147, 597-608.

Boone, David R. et al., "Bergey's Manual of Systematic Bacteriology—Second Edition—vol. One" The Archaea and the Deeply Branching and Phototrophic Bacteria, Springer, 4 pages.

Boopathy, R., "Anaerobic degradation of No. 2 diesel fuel in the wetland sediments od Barataria-Terrebone estuary under various electron acceptor conditions," Bioresource Technology 2003, vol. 86, pp. 171-175.

Brockman, Fred "Regulation of Microbial Communities" at http://www.sysbio.org/sysbio/microbial/index.stm, 2005, 2 pages.

Brown, L.R., and Vadie, A.A., "Slowing Production Decline and Extending the Economic Life of an Oil Field: New MEOR Technology", SPE 59306; SPE/DOE Improved Oil Recovery Symposium, Tulsa, Oklahoma, Apr. 3-5, 2000.

Budwill, Karen "Microbial Methanogenesis and its Role in Enhancing Coalbed Methane Recovery" (Canadian Coals) CSEG Recorder (Nov. 2003) pp. 41-43.

Business Wire, "U.S. Microbics opens new profit centr to outside customers; Bug factory brews microbe colonies for third party applications," Apr. 26, 2005, p. 1, 4 pgs.

(56) References Cited

OTHER PUBLICATIONS

Cervantes, Francisco J. et al, "Competition between methanogenesis and quinone respiration for ecologically important substrates in anaerobic consortia" FEMS Microbiology Ecology 34, 2000, pp. 161-171.
Claypool, George E. et al. "The Origin and Distribution of Methane in Marine Sediments" Natural Gases in Marine Sediments, Ed. Isaac R. Kaplan, 1974, pp. 99-139.
Claypool, Geroge E. "Geochemical Characterization of Biogenic Gas and Coalbed Methane in Shallow Gas Fields: Eastern Denver Basin, Powder River Basin and Williston Basin" Luca Technologies, Inc. Internal Report, Jul. 8, 2001, 29 pages.
Clayton et al. "Oil-Generating Coals of the San Juan Basin, New Mexico and Colorado, U.S." Org. Geochem. 1991, pp. 735-742, vol. 17, No. 6.
Clayton, C. et al. "Source Volumetrics of Biogenic Gas Generation" Bacterial Gas, Ed. R. Vially, 1992, pp. 191-204, Paris.
Coates, John D., Anderson, Robert T., et al., "Anaerobic Hydrocarbon Degradation in Petroleum-Contaminated Harbor Sediments under Sulfate-Reducing and Artificially Imposed Conditions", Environ. Sci. Technol., vol. 30, No. 9, pp. 2784-2789, 1996.
Connan, J. et al. Anaerobic biodegradation of petroleum in reservoirs: a widespread phenomenon in nature: 18th International Meeting on Organic Geochemistry Sep. 22-26, 1997 Maastricht, The Netherlands (Abstr.), p. O2: 5-6.
Connan, J. et al. "Origin of Gases in Reservoirs" 1995 International Gas Research Conference, 1996, pp. 21-41.
Conrad, R. "Contribution of hydrogen to methane production and control of hydrogen concentrations in methanogenic soils and sediments" FEMS Microbiology Ecology, 28 (1999) pp. 193-202.
DeBruin, R.H. et al. "Coalbed Methane in Wyoming" Wyoming State Geological Survey (Laramie, WY), Information Pamphlet 7 (second revision), 2004, 24 pages.
Donaldson et al., "Conference Focuses on Microbial Enhancement of Oil Recovery," The Oil and Gas Journal, pp. 47-52, Dec. 20, 1982.
Donaldson, Eric C. et al. Microbial Enhanced Oil Recovery, Developments in Petroleum Science, 1989, v. 22, pp. 1-14, 121, 123, 149, Elsevier.
Elias, Paul, "Mining for single-celled gold; Biotechs looking for cash in on Mother Nature's creations" Jul. 4, 2004, San Antonio Express-News, p. 3L, 3 pgs.
Faber, E. et al. "Distinction of Bacterial and Thermogenic Hydrocarbon Gases" Bacterial Gas, Ed. R. Vially, 1992, pp. 63-74, Paris.
Ferry et al. 1976. Anaerobic Degradation of Benzoate to Methane by Microbial Consortium. Arch. Microbiol. 107, pp. 33-40.
Ficker et al., "Molecular Characterization of a Toluene-Degrading Methanogenic Consortium," Applied and Enviromental Microbiology, Dec. 1999, vol. 65, pp. 5576-5585.
Flesner, R. et al. "Pilot-scale base hydrolysis processing of HMX-based plastic-bonded explosives", 4th International Symposium on Special Topics in Chemical Propulsion: Challenges in Propellants and 100 Years After Nobel, May 27-31, 1996, pp. 213-220.
Flesner, R. et al. "Pilot-scale base hydrolysis processing of HMX-based plastic-bonded explosives", Chemical Abstracts, vol. 130, No. 5, Feb. 1, 1998, Columbus, Ohio, U.S.; Abstract No. 54464a, pp. 835.
Gaasterland, Terry "Archaeal Genomics" Current Opinions in Microbiology (1999) 2:542-547.
Galagan, James, E. et al. "The Genome of M. acetivorans Reveals Extensive Metabolic and Physiological Diversity" Genome Research 12: 532-542 (2002).
Ravot, G. et al., "Fusibacter Paucivorans Gen. Nov., Sp. Nov., an Anaerobic, Thiosulfate-Reducing Bacterium From an Oil-Producing Well," International Journal of Systematic Bacteriology (1999) 49, 1141-1147.
Grbic-Galic, D., and Vogel, T. "Transformation of Toluene and Benzene by mixed methanogenic cultures" Applied and Environmental Microbiology, 1987, v. 53, pp. 254-260.
Groudeva, V. I. et al. "Enhanced Oil Recovery by Stimulating the Activity of the Indigenous Microflora of Oil Reservoirs": Biohydrometallurgical Technologies (Eds. Torma, A. E., Apel, M.L.; and Brierlay, C.L.): Minerals, Metals, & Mater. Soc. Biohydromet. Technol. Int. Symp, 1993 (Jackson Hole, Wy. 93.8.22-25) Proc., v. 2, pp. 349-356.
Gullapalli, Irene L. et al., "Laboratory Design and Field Implementation of Microbial Profile Modification Process", SPE Reservoir Evaluation & Engineering, v. 3, No. 1, pp. 42-49, Feb. 2000.
Halbouty, M.T. "East Texas Field—USA, East Texas Basin, Texas; in Stratigraphic Traps II" (compiled by N.H. Foster, and E.A. Beaumont) AAPG Treatise of Petroleum Geology, Atlas of Oil and Gas Fields, 1991, pp. 189-206.
Hales, B.A. et al. "Isolation and Identification of Methanogen-specific DNA from Blanket Bog Peat by PCR Amplification and Sequence Analysis", Applied and Environmental Microbiology, 1996, pp. 668-675.
Hattori, Satoshi et al.; "*Thermacetogenium phaeum* gen.nov.,sp.nov., a strictly anaerobic, thermophilic, syntrophic acetate-oxidizing bacterium", Internation. Journal of Systematic and Evolutionary Microbiology (2000), 50, 1601-1609, 9 pages, 2000.
Hermann, M. et al. "Anaerobic Microflora of Oil Reservoirs: Microbiological Characterization of Samples from Some Production Wells" Bacterial Gas (R. Vially Ed.) Editions Technip. Paris, 1992, pp. 223-233.
Hunkeler et al., "Petroleum Hydrocarbon Mineralization in Anaerobic Laboratory Aquifer Columns," Journal of Contaminant Hydrology 32, pp. 41-61, 1998.
Intera In. and Naval Facilities Engineering Service Center; *Surfactant-Enhanced Aquifer Remediation (SEAR) Implementation Manual*; NFESC Technical Report TR-2219-ENV, Apr. 2003, pgs: entire document; Naval Facilities Engineering Command Washington, DC 20374-5065 USA.
Ivanov, M. V. et al. "Additional Oil Production During Field Trials in Russia: Microbial Enhancement of Oil Recovery—Recent Advances" (4th US DOE MEOR Int Conf (Upton, NY, 1992) Proc; Elsevier Develop Petrol Sci Ser No. 39), 1993, pp. 373-381.
Ivanov, M. V. et al. "Die mikrobiologische Bildung von Methan in einer abzubauenden Erdollagerstatte" Frieberger Forschungshefte Reihe C, v., 1982, vol. 389, pp. 189-199.
Johnson et al., 1991, "Preliminary Results of a Coalbed Methane Assessment of the Wind River Indian Reservation, Whoming" Coalbed Methane, pp. 273-284.
Johnson, Ronald C. et al. "A Preliminary Evaluation of Coalbed Methane Resources of the Wind River Indian Reservation, Wyoming" Coal-Bed Methane Potential of the Wind River Indian Reservation, Ed. Stephen Manydeeds, Dec. 1991, pp. 40-64, Bureau of Indian Affairs Division of Energy and Mineral Resources.
Kasting, James F. "When Methane Made Climate" Scientific American, Jul. 2004, pp. 80-85.
Wantabe, K. et al., "Diversity and Abundance of Bacteria in an Underground Oil-Storage Cavity," BMC Microbiology, pp. 1-10.
Kim, Ann G. "Experimental Studies on the Origin and Accumulation of Coalbed Gas" U.S. Dept. of the Interior Bureau of Mines, Report of Investigations 8317, 1978, 18 pages.
Kim, Ann G. et al. "Hydrocarbon Gases Produced in a Simulated Swamp Environment" U.S. Dept. of the Interior Bureau of Mines, Report of Investigations 7690, 1972, 13 pages.
Klein, A. et al. "Comparative Analysis of Genes Encoding Methyl Coenzyme M Reductase in Methanogenic Bacteria", Mol Gen Genet, 1988, 213:409-420.
Krumholtz, Lee R. et al. "Confined subsurface microbial communities in Cretaceous Rock" Nature (Mar. 6, 1997) pp. 64-66.
Kunzig, Robert "20,000 Microbes Under the Sea" Mar. 2004, pp. 32-41, vol. 25, No. 3.
Law, Ben E. et al "Coalbed Gas Accumulations in the Paleocene Fort Union Formation, Powder River Basin, Wyoming" Coalbed Methane—1991; Rocky Mountain Association of Geologists, pp. 179-190.
Le Blanc, Leonard, Artificial Recharge, Offshore, p. 10, Feb. 2000.
L'Haridon, S., Reysenbach, A.L., et al., Hot Subterranean Biosphere in a Continental Oil Reservoir, Nature, v. 377, pp. 223-224, Sep. 21, 1995.
Li, M. et al. "Advances in Simulated Tests of Biogas" Oil & Gas Geology, 1996, v. vol. 17, No. 2, pp. 117-122, with abstract.

(56) References Cited

OTHER PUBLICATIONS

Lollar, B. Sherwood et al. "Evidence for bacterially generated hydrocarbon gas in Canadian Shield and Fennoscandian Shield rocks" Geochemicaet Cosmochimica Acta vol. 57, pp. 5073-5085 (1993).

Lomans, Bart P. et al. "Isolation and Characterization of *Mehanomethylovorans hollandica* gen. nov., sp. nov., Isolated from Freshwater Sediment, a Methyltrophic Methanogen Able to Grow on Dimethyl Sulfide and Methanethiol." Applied and Env. Microbiology, Aug. 1999, p. 3641-3650, vol. 65.

Lovely, Derek R. "Deep Subsurface Microbial Processes" Reviews of Geophysics, 33, Aug. 3, 1995, pp. 365-381.

Luo Hong-Wei et al: "Differential expression of methanogenesis genes of *Methanothermobacter thermoautotrophicus*(former *Methanobacterium* thermoautotrophicum) in pure culture and in cocultures with fatty acid-oxidizing syntrophs": Applied and Environmental Microbiology, vol. 68, No. 3, Mar. 2002, pp. 1173-1179, XPOO2551248 ISSN: 0099-2240.

Magot, Michel et al. "Microbiology of Petroleum Reservoirs" Antonie van Leeuwenhoek, 2000, 77: 103-116.

Mattavelli, L. et al. "Deep Isotopic Light Methane in Northern Italy" Bacterial Gas, Ed. R. Vially, 1992, pp. 121-132.

McDonald, I.R. et al. "Molecular Ecological Analysis of Methanogens and Methanotrophs in Blanket Bog Peat" Microbial Ecology (1999) 38:225-233.

Menking et al., "Rapd Cleanup of Bacterial DNA from Field Samples", Elsevier, Resources, Conservation and Recycling 27 (1999), 179-186.

Middledorp et al., "Enrichment and Properties of a 1,2,4-trichlorobenzene-Dechlorinating Methanogenic Microbial Consortium," Applied and Environmental Microbiology, Apr. 1997, vol. 63, pp. 1225-1229.

Nandi, R et al. "Microbial Production of Hydrogen: An Overview" Critical Reviews in Microbiology, 24 (1): 61-84 (1998).

Nazina, T. N. et al. "Occurrence and Geochemical Activity of Microorganisms in High-Temperature, Water-Flooded Oil Fields of Kazakhstan and Western Siberia" Geomicrobiology Journal, 1995, v. 13, pp. 181-192.

Nazina, T. N. et al. "Microbial Oil Transformation Processes Accompanied by Methane and Hydrogen-Sulfide Formation" Geomicrobiology Journal, 1985, vol. 4, No. 2, pp. 103-130.

Neue, Heinz-Ulrich "Methane Emission from Rice Fields", BioScience, 1993, pp. 466-473, vol. 43, No. 7, downloaded from http://www.ciesin.org/docs/004-032/004-032.html.

Ng, T. K., and Weimer, P. J., "Possible Nonanthropogenic Origin of Two Methanogenic Isolates from Oil-Producing Wells in the San Miguelito Field, Ventura County, California", Geomicrobiology Journal, 1989, v. 7, pp. 185-192.

O'Carroll, Christopher "The Pervasive Presence of Microbes" http://www/umassmag.com/Summer_2003/The_pervasive_presence_of_microbes_5_08.html, 2003, 3 pages.

Ooteghem et al., "Hydrogen Production by the Thermophilic Bacterium, Thermotogo Neapolitana," Proceedings of the 2001 DOE Hydrogen Program Review, 2001, pp. 1-12.

Orphan et al., "Culture-Dependant and Culture-Independent Characterization of Microbial Assemblages Associated with High-Temperature Petroleum Reservoirs," American Society for Microbiology, pp. 700-711, 2000.

Panow, A. et al. "Mechanisms of Biologically-Mediated Methane Evolution from Black Coal", Fuel Processing Technology v. 52, pp. 115-125, 1997.

Pedersen, K. "Exploration of Deep Intraterrestrial Microbial Life: Current Perspectives" FEMS Microbiology Letters 185 (2000) pp. 9-16.

Potter et al. "Artificial Recharge," Offshore, Feb. 2000, pp. 10.

Pun et al. "Enhanced Coalbed Methane Recovery" Proceedings 1990 SPE Annual Technical Conference and Exhibition Reservoir Engineering, Sep. 23-26, 1990, New Orleans, Louisiana, SPE 20732, 1990, pp. 193-202.

Rahman et al., "Towards efficient Crude Oil Degradation by a mixed bacterial consortium," Bioresource Technology, 2002, vol. 85, pp. 257-261.

Reeve, John N. "Archaebacteria Then . . . Archaes Now (Are There Really No Archaeal Pathogens?)" Journal of Bacteriology, vol. 181, No. 12, Jun. 1999 pp. 3613-3617.

Revesz, K. et al. "Methane production and consumption monitored by stable H and C isotope ratios at a crude oil spill site, Bemidji, Minnesota" Applied Geochemistry, 1995, vol. 10, pp. 505-515.

Rice, Dudley D. "Controls, habitat, and resource potential of ancient bacterial gas", Bacterial Gas, Ed. Vially, R., 1992, pp. 91-118, Paris.

Rice, Dudley D. et al. "Characterization of coal-derived hydrocarbons and source-rock potential of coal beds, San Juan Basin, New Mexico and Colorado, U.S.A." International Journal of Coal. Geology, 1989, pp. 597-626, vol. 13.

Rice, Dudley D. et al. "Composition and Origins of Coalbed Gas" Hydrocarbons from Coal: American Association of Petroleum Geologists Studies in Geology #38, Eds. Law, B.E., and Rice, D.D., 1993, pp. 159-184.

Rice, Dudley D. et al. "Generation, Accumulation, and Resource Potential of Biogenic Gas" The American Association of Petroleum Geologists Bulletin, vol. 65, No. 1, Jan. 1981.

Rice, Dudley D. et al. "Identification and Significance of Coal-Bed Gas, San Juan Basin, Northwestern New Mexico and Southwestern Colorado" Geology and Coal-Bed Methane Resources of the Northern San Juan Basin, Colorado and New Mexico, Ed. J. Fassett, Coal-Bed Methane, San Juan Basin, 1988, pp. 51-59, Rocky Mountain Association of Geologists.

Rice, Dudley D. et al. "Nonassociated Gas Potential of San Juan Basin Considerable" Oil & Gas Journal, Aug. 1990, pp. 60-61, vol. 88, No. 33.

Ridgley, J.L. et al. "Re-Evaluation of the Shallow Biogenic Gas Accumulation, Northern Great Plains, USA—Is the Similar Gas Accumulation in Southeastern Alberta and Southwestern Saskatchewan a Good Analog?" Summary of Investigations (1999) vol. 1 pp. 64-78.

Rightmire, C.T. et al. "Coalbed Methane Resource", 1984, Coalbed methane resources of the United States, AAPG Studies in Geology #17, Tulsa, p. 1-B.

Rooney-Varga, Juliette N. et al. "Microbial Communities Associated with Anaerobic Benzene Degradation in a Petroleum-Contaminated Aquifer", Applied and Environmental Microbiology, v. 65, No. 7, pp. 3056-3063, Jul. 1999.

Rozanova, E.P. et al. "Distribution of Sulfate-Reducing Bacteria Utilizing Lactate and Fatty Acids in Anaerobic Ecotopes of Flooded Petroleum Reservoirs" Institute of Microbiology, Academy of Sciences of the USSR, Moscow. Translated from Mikrobiologiya, vol. 60, No. 2, pp. 360-367, Mar.-Apr. 1991.

Rozanova, E.P. et al. "Microbiological Processes in a High-Temperature Oil Field", Microbiology, v. 70, No. 1, pp. 102-110, 2000.

Schoell, Martin "Genetic Characteristics of Natural Gases" The American Association of Petroleum Geologists Bulletin, Dec. 1983, p. 2225-2238, vol. 67, No. 12.

Schoell, Martin et al. "Natural Sites of Bio-Conversion of CO2 and Hydrocarbons in the Subsurface: San Juan Basin and Michigan Basin" 2001 AAPG Annual Convention, Jun. 3-6, 2001, p. A180, abstract only.

Scott, A.R., Intergas'95, "Limitations and Benefits of Microbiallly Enhanced Coalbed Methane"; May 15-19, 1995—The University of Alabama Tuscaloosa, 10 pages, 1995.

Scott, Andrew R. "Composition and Origin of Coalbed Gases from Selected Basins in the United States" Proceedings of the 1993 International Coalbed Methane Symposium, University of Alabama/Tuscaloosa, May 17-21, 1993; pp. 207-222.

Scott, Andrew R. "Improving Coal Gas Recovery with Microbially Enhanced Coalbed Methane" in Coalbed Methane: Scientific, Environmental and Economic Evaluation; Eds. M. Mastaletcz, M. Glikson, and S. Golding, 1999, pp. 89-110, Kluwer Academic Publishers, Netherlands.

Scott, Andrew R. "Review of Key Hydrogeological Factors Affecting Coalbed Methane Producibility and Resource Assessment" Oklahoma Coalbed-Methane Workshop, 1999, pp. 12-36.

(56) References Cited

OTHER PUBLICATIONS

Scott, Andrew R. et al. "A New Energy Resource: Microbially Enhanced Gas Generation" 2001 AAPG Annual Convention, Jun. 3-6, 2001, p. A182, abstract only.

Scott, Andrew R. et al. "Composition, distribution, and origin of Fruitland Formation and Pictured Cliffs Sandstone gases, San Juan basin, Colorado and New Mexico", in S.D. Schwochow, D.K. Murray, and M.F. Fahy, eds., Coalbed methane of western North America: Denver, Rocky Mountain Association of Geologists, 1991, p. 93-108.

Scott, Andrew R. et al. "Limitations and Benefits of Microbially Enhanced Coalbed Methane" International Unconventional Gas Symposium (INTERGAS), May 15-19, 1995; pp. 423-432.

Scott, Andrew R. et al. "Microbially Enhanced Coalbed Methane: Limitations and Possible Benefits" AAPG Convention, 1995, p. 86A, abstract only.

Scott, Andrew R. et al. "Relation between basin hydrology and Fruitland gas composition, San Juan Basin, Colorado and New Mexico" Methane From Coal Seams Technology, Nov. 1991, pp. 10-18, vol. 9, No. 1.

Scott, Andrew R. et al. "Thermogenic and Secondary Biogenic Gases, San Juan Basin, Colorado and New Mexico—Implications for Coalbed Gas Producibility" AAPG Bulletin, Aug. 1994, v. 78, No. 8, pp. 1186-1209.

Smith, John W. et al. "Microbial Origin of Australian Coalbed Methane" AAPG Bulletin, vol. 80, No. 6 (Jun. 1996), pp. 891-897.

Smith, John W. et al. "The Stable Isotope Geochemistry of Australian Coals" Org. Geochem. vol. 3, 1982, pp. 111-131.

Springer, E. et al. "Partial Gene Sequences for the A Subunit of Methyl-Coenzyme M Reductase (Mcrl) as a Phylogenetic Tool for the Family Methanosarcinaceae", International Journal of Systematic Bacteriology, 1995, pp. 554-559.

Takashima, M. et al. "Mineral Requirements for Methane Fermentation" Critical Reviews in Environmental Control, vol. 19, Issue 5 (1990) pp. 465-479.

Um, Y., "Isolation and characterization of polycyclic aromatic hydrocarbon-degrading microorganisms under methanogenic conditions," Dissertation, Universtity of Maryland, 2004, pp. 1-99.

Velji, M.I. et al., "The Dispersion of Adhered Marine Bacteria by Pyrophsphate and Ultrasound Prior to Direct Counting", published in IFREMER, Actes de Colloques, 3, 1986, pp. 249-259.

Volkwein, J.C. et al. "Biological Production of Methane from Bituminous Coal", Fuel Processing Technology, v. 40, pp. 339-345, 1994.

Weiner, J. M., and Lovley, D. R. "Rapid Benzene Degradation in Methanogenic Sediments from a Petroleum-Contaminated Aquifer", Appl. Environ. Microbiology 1998, vol. 64, No. 5, pp. 1937-1939.

Wellsbury, Peter et al. "Deep Marine biosphere fuelled by increasing organic matter availability during burial and heating" Nature 388, 573-576 (Aug. 7, 1997).

Whitfield, John "Origins of life: Born in a watery commune" Nature, (Feb. 19, 2004) pp. 674-676, vol. 427.

Whiticar, Michael J. "Correlation of natural gases with their sources" In: Magoon L. and W. Dow (eds.) The Petroleum System From Source to Trap, AAPG Spec. Publ. Memoir 60, 1994, Ch. 16, 261-83.

Whiticar, Michael J. et al. "Biogenic methane formation in marine and freshwater environments: CO2 reduction vs. acetate fermentation—Isotope evidence" Geochimica et Cosmochimica Acta, 1986, pp. 693-709, vol. 50, No. 5.

Zengler et al. "Methane Formation From Long-Chain Alkanes by Anaerobic Microorganisms," Nature, vol. 401, pp. 266-269, Sep. 16, 1999.

Zobell, C.E., "Bacterial Release of Oil From Sedimentary Materials," The Oil & Gas Journal, pp. 62-65, Aug. 2, 1947.

Gilcrease, P., et al., "Making microbial methane work: The potential for new biogenic gas," WorldOil, Nov. 2007 [retrieved on Aug. 8, 2011], 7 pages, vol. 228 No. 11, retrieved from http://www.worldoil.com/November-2007-Making-microbial-methane-work-The-potential-for-new-biogenic-gas.html.

Author Unknown, "Chapter 4: Hydraulic Fracturing Fluids," Evaluation of Impacts to Underground Sources of Drinking Water by Hydraulic Fracturing of Coalbed Methane Reservoirs, U.S. Environmental Protection Agency, Jun. 2004, 26 pages.

Batelle and Duke Engineering and Services; *Surfactant-Enhanced Aquifer Remediation (SEAR) Design Manual*; NFESC Technical Report TR-2206-ENV, Apr. 2002, 110 pgs: entire document; Naval Facilities Engineering Command Washington, DC 20374-5065 USA.

Brauer, S. et al., "Methanogenesis in McLean Bog, an Acidic Peat Bog in Upstate New York: Stimulation by H2/CO2 in the Presence of Rifampicin, or by Low Concentrations of Acetate," (*Geomicrobiology Journal*, Oct.-Nov. 2004, vol. 21, No. 7, pp. 433-443(11)), http://www.ingentaconnect.com, printed Apr. 26, 2005, 2 pgs.

Braun, Harry, "The Bad News About Natural Gas," Hydrogen News, Mar. 15, 2003, 2 pgs.

CAN Europe, "Climate technology sheet #9: Hydrogen production," published Nov. 2003, pp. 1-10.

Dong, Wen-Sheng et al., "Hydrogen Production from Methane Reforming Reactions over Ni/MgO Catalyst," Bull. Korean Chem. Soc. 2001, vol. 22, No. 12, Aug. 11, 2001, 1 pg.

Dumitru, Razvan et al., "Targeting Methanopterin Biosynthesis to Inhibit Methanogenesis," Applied and Environmental Microbiology, vol. 69, No. 12, Dec. 2003, pp. 7236-7241.

Hydrogen production in oil field production fluids with inactive methanogens. Data to be considered for incorporation into Luca's hydrogen patent, unauthored text, Mar. 9, 2005, 2 pgs.

Karl Lang, "*Coalbed Methane Trends*," PTTC State-of-the-Art Technology Summary, Excerpts in PTTC Network News, 2nd Quarter 2000, http://www.pttc.org/tech_sum/statev6no2.htm, printed Mar. 26, 2004, pp. 1-6.

Lovley, Derek R. et al., "Use of Dissolved H2 Concentrations to Determine Distribution of Microbially Catalyzed Redox Reactions in Anoxic Groundwater," ES&T Research, Eviron. Sc. Technol., vol. 28, No. 7, 1994, pp. 1205-1210.

PCT International Search Report and Written Opinion mailed May 5, 2010; International Application No. PCT/US2010/028691; 12 pages.

Ulrich, Glenn A. et al., "Active Biogenesis", *Energy*, Spring 2005, XP008128250, pp. 21-26.

Zajic, J. E. et al., "Microbial Hydrogen Production From Replenishable Resources," Int. J. Hydrogen Engergy, vol. 4, published 1979, pp. 385-402.

Van Ginkel, S., et al., "Biohydrogen Production as a Function of pH and Substrate Concentration", Environmental Science and Technology, American Chemical Society, Easton, PA, USA, vol. 35, No. 24, Dec. 15, 2001, pp. 4726-4730.

EP Supplementary Search Report mailed Oct. 12, 2010; Application No. 05747464.5; 7 pages.

Author Unknown, "Climate technology sheet #9: Hydrogen production," Climate Action Network Europe, 2003, 10 pages.

Boone, D., et al., Bergeys Manual of Systematic Bacteriology—Second Edition—vol. One "The Archaea and the Deeply Branching and Phototrophic Bacteria", 2001, Springer, 4 pages.

Wantanabe, K., et al., "Diversity and Abundance of Bacteria in an Underground Oil-Storage Cavity." BMC Microbiology, [online], 2002, [retrieved on Aug. 18, 2011]. Retrieved from: http://www.biomedcentral.com/content/pdf/1471-2180-2-23.pdf.

Zajic, J., et al., "Microbial Hydrogen Production From Replenishable Resources," Int. J. Hydrogen Energy, 1979, vol. 4, pp. 385-402.

* cited by examiner

CHEMICAL AMENDMENTS FOR THE STIMULATION OF BIOGENIC GAS GENERATION IN DEPOSITS OF CARBONACEOUS MATERIAL

CROSS-REFERENCES TO RELATED APPLICATIONS

This application is a divisional of U.S. patent application Ser. No. 11,399,099, filed Apr. 5, 2006, the entire disclosures of which are incorporated hereby by reference for all purposes.

BACKGROUND OF THE INVENTION

Increasing world energy demand is creating unprecedented challenges for recovering energy resources, and mitigating the environmental impact of using those resources. Some have argued that the worldwide production rates for oil and domestic natural gas will peak within a decade or less. Once this peak is reached, primary recovery of oil and domestic natural gas will start to decline, as the most easily recoverable energy stocks start to dry up. Historically, old oil fields and coal mines are abandoned once the easily recoverable materials are extracted. These abandoned reservoirs, however, still contain significant amounts of carbonaceous material. The Powder River Basin in northeastern Wyoming, for example, is still estimated to contain approximately 1,300 billion short tons of coal. Just 1% of the Basin's remaining coal converted to natural gas could supply the current annual natural gas needs of the United States (i.e., about 23 trillion cubic feet) for the next four years. Several more abandoned coal and oil reservoirs of this magnitude are present in the United States.

As worldwide energy prices continue to rise, it may become economically viable to extract additional oil and coal from these formations with conventional drilling and mining techniques. However, a point will be reached where more energy has to be used to recover the resources than can be gained by the recovery. At that point, traditional recovery mechanisms will become uneconomical, regardless of the price of energy. Thus, new recovery techniques are needed that can extract resources from these formations with significantly lower expenditures of energy and costs.

One route for light hydrocarbon recovery that has received little commercial attention is biogenic conversion of carbonaceous materials in geologic formations into methane. As noted above, large potential sources of methane and other hydrocarbons with enhanced hydrogen content are locked up in the carbonaceous materials in coal, residual oil, etc. In biogenic conversion, microorganisms in the formation treat these carbonaceous materials as a food source and metabolize them into metabolic intermediates and products, such as alcohols, organic acids, aromatic compounds, hydrogen and methane, among others.

In many formations, however, the environmental chemistry does not favor the biogenic production of metabolic products like hydrogen and methane. In some of these formations, the presence of an inhibitor (e.g., saline) can prevent the microorganisms from metabolizing the carbonaceous substrate into the products. In other formations, the low concentration of one or more compounds (e.g., nutrient compounds) in the formation environment can slow or stop biogenic production of the products. In still other formations, a rise in concentration of a metabolic intermediate or product generated by an active consortium of microorganisms can slow additional metabolic activity.

Thus, there remains a need to identify chemical compounds that effect the rate of biogenic production of metabolic products by microorganisms in a formation environment. There also remains a need for methods of introducing chemical amendments to a geologic formation that will stimulate the biogenic production of the metabolic products. These and other needs are addressed by the present invention.

BRIEF SUMMARY OF THE INVENTION

Embodiments of the invention include methods of stimulating biogenic production of a metabolic product with enhanced hydrogen content. The methods may include accessing a consortium of microorganisms in a geologic formation that includes a carbonaceous material. The methods may also include providing hydrogen and one or more phosphorous compounds to the microorganisms. The combination of the hydrogen and phosphorous compound stimulates the consortium to metabolize the carbonaceous material into a metabolic product with enhanced hydrogen content.

Embodiments of the invention also include additional methods of stimulating biogenic production of a metabolic product with enhanced hydrogen content. The methods may include accessing a consortium of microorganisms in a geologic formation that includes a carbonaceous material and providing a carboxylate compound to the microorganisms. The carboxylate compound stimulates the consortium to metabolize carbonaceous material in the formation into the metabolic product with enhanced hydrogen content.

Embodiments of the invention still also include methods of activating a consortium of microorganisms in a geologic formation to produce a metabolic product with enhanced hydrogen content. The methods may include accessing the consortium in the formation, and providing an acetate compound to the microorganisms. The acetate compound activates the consortium to metabolize carbonaceous material in the formation into the metabolic product with enhanced hydrogen content.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

DETAILED DESCRIPTION OF THE INVENTION

Methods of stimulating the production of metabolic products with enhanced hydrogen content (e.g., gases such as hydrogen and methane) through chemical amendments are described. The amendments stimulate a consortium of microorganisms in a geologic formation to metabolize carbonaceous material in the formation into the metabolic products. The stimulation effects of the amendments may include increasing the rate of production of a metabolic intermediary and/or the metabolic product. They may also include activating a consortium in the formation to start producing the metabolic products. They may further include stopping or decreasing a "rollover" effect such as when the concentration of one or more metabolic products starts to plateau after a period of monotonically increasing. These and other stimulation effects may be promoted by the chemical amendments that are introduced by the methods of the invention.

Figure 1:
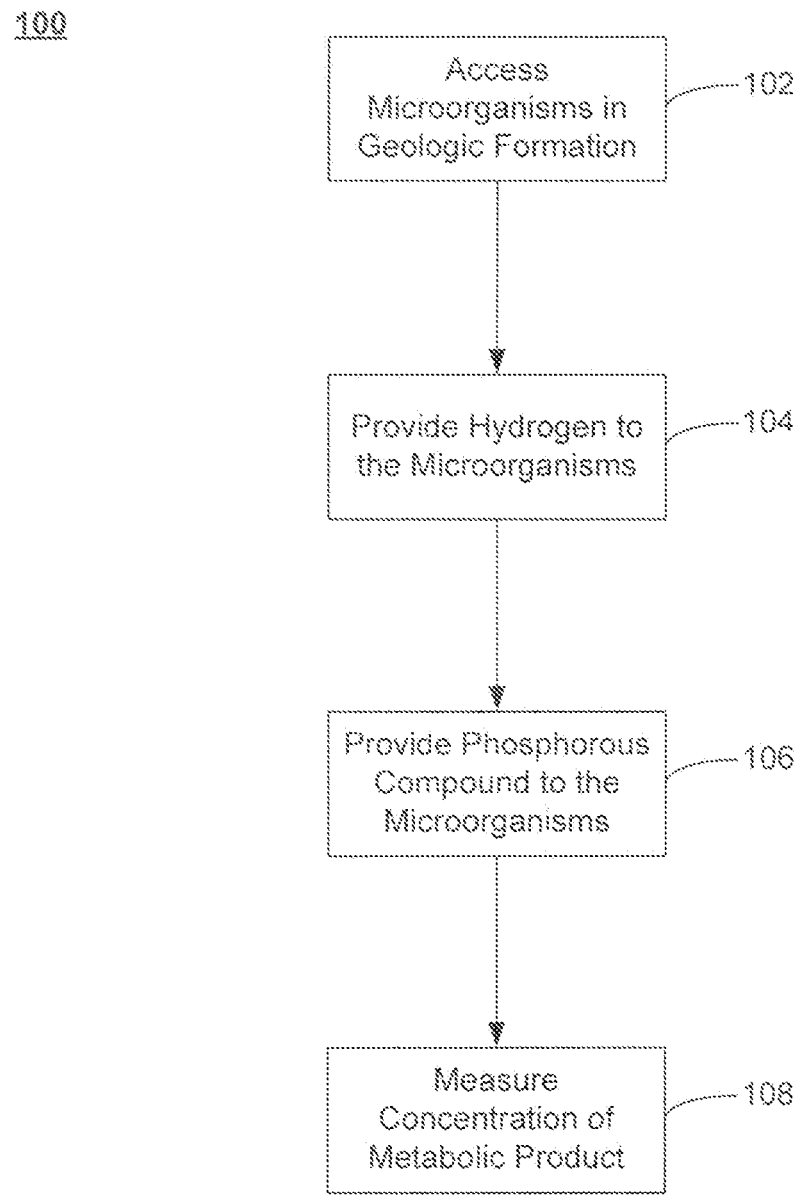
FIG. 1 is a flowchart illustrating a method of introducing hydrogen and phosphorous amendment to microorganisms in geologic formations according to embodiments of the invention.

Referring now to FIG. 1, a flowchart illustrating a method 100 of introducing hydrogen and phosphorous amendments to microorganisms in a geologic formation according to embodiments of the invention is shown. The method 100 includes accessing the formation water 102 in the geologic formation. The geologic formation may be a previously explored, carbonaceous material-containing subterranean formation, such as a coal mine, oil field, natural gas deposit, carbonaceous shale, etc. In many of these instances, access to the formation can involve utilizing previously mined or drilled access points to the formation. For unexplored formations, accessing the formation may involve digging or drilling thorough a surface layer to access the underlying site where the microorganisms are located.

Once access to the microorganisms in the formation is available, an amendment may be provided to them. In method 100, providing the amendment may include providing hydrogen to the microorganisms 104. Providing the hydrogen 104 may involve the direct injection of hydrogen gas into the formation region were the microorganisms are located. Alternatively (or in addition) a liquid and/or aqueous hydrogen release compound may be provided to the formation. The compound can undergo a chemical or biochemical reaction in the formation that produces hydrogen gas in situ where the microorganisms reside. Examples of hydrogen release compounds may include polyacetate ester compounds that release lactic acid on contact with water. The lactic acid may then be metabolized by the microorganisms to produce organic acids (e.g., pyruvic acid, acetic acid, etc.) and hydrogen gas.

The amendment may also include providing one or more phosphorous compounds to the microorganisms 106. These phosphorous compounds may include phosphorous compounds (e.g., $PO_x$ compounds were x is 2, 3 or 4), such as sodium phosphate ($Na_3PO_4$) and potassium phosphate ($K_3PO_4$), as well as monobasic and dibasic derivatives of these salts (e.g., $KH_2PO_4$, $K_2HPO_4$, $NaH_2PO_4$, $Na_2HPO_4$, etc.). They may also include phosphorous oxyacids and/or salts of phosphorous oxyacids. For example, the phosphorous compounds may include $H_3PO_4$, $H_3PO_3$, and $H_3PO_2$ phosphorous oxyacids, as well as dibasic sodium phosphate and dibasic potassium phosphate salts. The phosphorous compounds may also include alkyl phosphate compounds (e.g., a trialkyl phosphate such as triethyl phosphate), and tripoly phosphates. The phosphorous compounds may further include condensed forms of phosphoric acid, including tri-polyphosphoric acid, pyrophosphoric acid, among others. They may also include the salts of condensed phosphoric acids, including alkali metal salts of tripolyphosphate (e.g., potassium or sodium tripolyphosphate), among other salts.

The hydrogen and phosphate may be provided to the formation in a single amendment, or they may be provided in separate stages. For example, if the phosphorous amendment takes the form of an aqueous solution, the solution may be injected into the formation with aid of compressed hydrogen gas. This allows the two components to be provided to the formation at substantially the same time. Alternatively, the hydrogen or phosphate amendment may be introduced first, followed by the introduction of the other compounds.

Whether the hydrogen and phosphorous compounds are introduced to the formation simultaneously or separately, they will be combined in situ and exposed to microorganisms. The combination of the hydrogen and phosphorous compound(s) can stimulate the microorganisms to metabolize carbonaceous material in the formation into metabolic products with enhanced hydrogen content, like methane. The enhanced hydrogen content products have a higher mol. % of hydrogen atoms than the starting carbonaceous material. For example, methane, which has four C—H bonds and no C—C bonds, has a higher mol. % hydrogen than a large aliphatic or aromatic hydrocarbon with a plurality of C—C single and double bonds. Additional details about compounds with enhanced hydrogen content may be found in co-assigned U.S. patent application Ser. No. 11/099,881, to Pfeiffer et al, filed Apr. 5, 2005, and entitled "GENERATION OF MATERIALS WITH ENHANCED HYDROGEN CONTENT FROM ANAEROBIC MICROBIAL CONSORTIA" the entire contents of which is herein incorporated by reference for all purposes.

Method 100 may further include adding additional amendments to the to formation. For example, a yeast extract amendment may be added to provide nutrients to the microorganisms in the formation. The yeast extract may include digests and extracts of commercially available brewers and bakers yeasts.

Method 100 may also include measuring the concentration of a metabolic product 108. For gas phase metabolic products, the partial pressure of the product in the formation may be measured, while aqueous metabolic products may involve measurements of molar concentrations. FIG. 1 shows the measurement of metabolic products being made after the introduction of the hydrogen and phosphorous amendment. Measurements may also be made before providing the amendment, and a comparison of the product concentration before and after the amendment may also be made.

Figure 2:
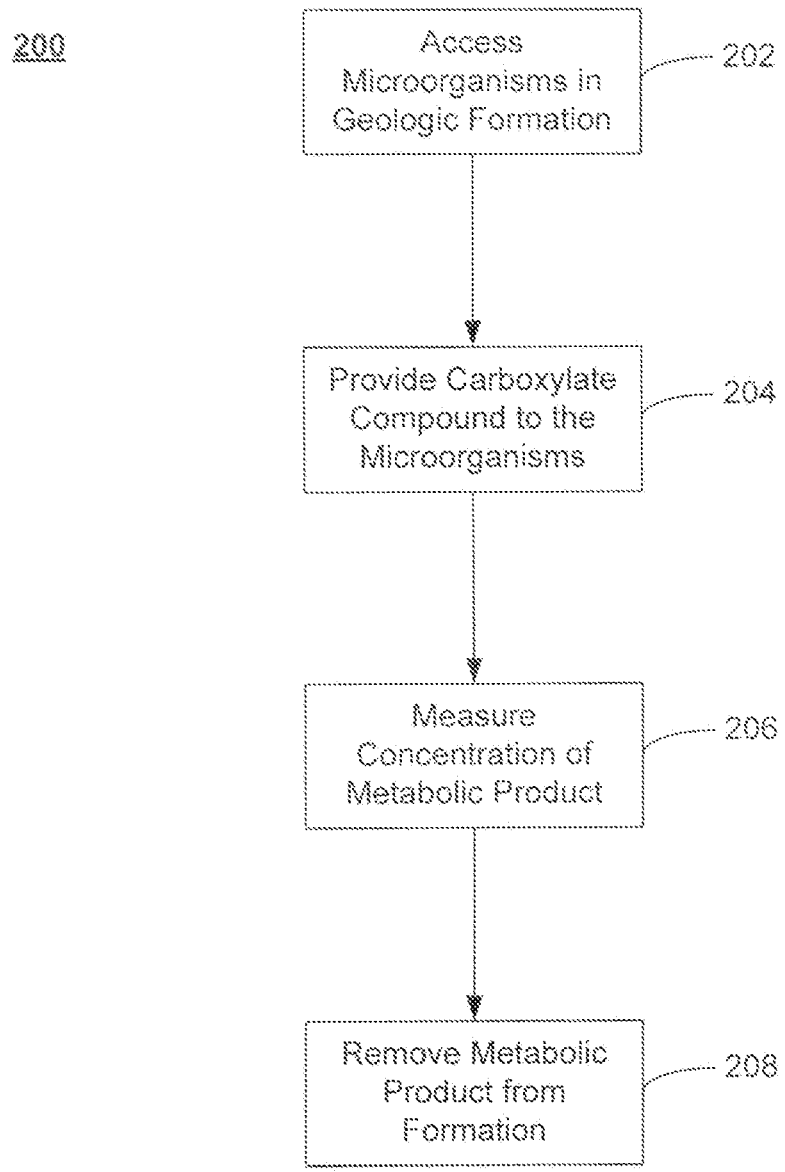
FIG. 2 is a flowchart illustrating a method of introducing carboxylate compound amendment to microorganisms in geologic formations according to embodiments of the invention.

FIG. 2 shows a method 200 of introducing a carboxylate compound amendment to microorganisms in geologic formations according to embodiments of the invention. The method 200 may include accessing the microorganism in the geologic formation 202. Once access is gained, one or more carboxylate compounds may be provided to the microorganisms in situ 204. The carboxylate compound may be an organic compound having one or more carboxylate groups (e.g., $COO^-$ groups). These compounds are typically organic acids or their salts. Examples include salts of acetate (i.e., $H_3CCOO^-$); benzoate (i.e., $Ph\text{-}COO^-$, where Ph is a phenyl group); and formate (i.e., $HCOO^-$), among other carboxylate groups. Additional amendments, such as a yeast extract amendment that provides nutrients to the microorganism in the formation, may also be provided.

The concentration of a metabolic product may be measured 206 following the introduction of the carboxylate compound. The product concentration may also be measured before the carboxylate compound is introduced, to determine the effect of adding the compound. In some instances, introducing the carboxylate compound to the microorganisms may cause an almost immediate increase in the production rate of the metabolic product. In other instances, there may be a period of delay between the introduction of the carboxylate compound and an increase in the production of the metabolic product. For example, the concentration of the metabolic product in the formation may stay at pre-introduction levels for about 30, 40, 50, 60, 70, or 80 days or more before significantly increasing.

A delay of several days or months between introducing the carboxylate compound and measuring a increase in the production of the metabolic product may be called the activation period. During this time, the presence of the carboxylate compound(s) may be influencing the population or metabolic pathways of the microorganisms. Very little (or even none) of the carboxylate compound may be metabolized by the microorganisms during the activation period. In these instances, the carboxylate compound may be acting as a catalyst that activates a metabolic pathway for the production of the metabolic product. Multiple introductions of the amendment may be made over the course of the activation period to maintain a concentration level of the amendment in the formation. Alternatively, the amendment can be pulsed into the formation using discontinuous injections. Experiments demonstrating activation of methane production with an acetate amendment are described in the Experimental section below.

Method 200 may also include removing the metabolic product 208 building up in the formation as a result of the carboxylate compound amendment. If the metabolic product is a gas such as hydrogen or methane, it may be removed with conventional natural gas recovery equipment. In some examples, the products may be removed through the same access points that were used to provide the carboxylate compound to the microorganisms. In additional examples, the products may be forced out of the formation by injecting a displacement fluid (e.g., nitrogen, water, etc.) into the formation.

Figure 3:
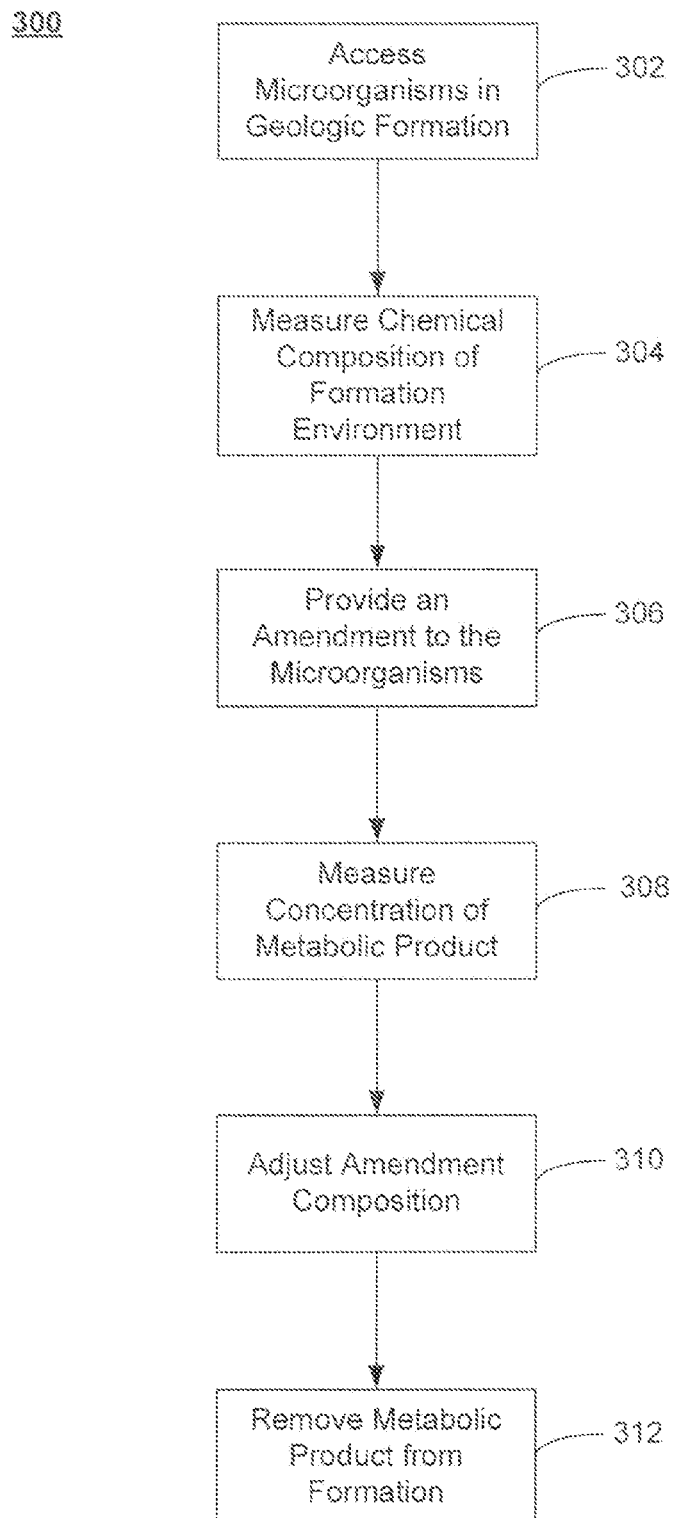
FIG. 3 is a flowchart illustrating a method of measuring the effects of introduced amendments on the production of metabolic products from geologic formations according to embodiments of the invention.

Referring now to FIG. 3, a flowchart illustrating a method 300 of measuring the effects of introduced amendments on the production of metabolic products from geologic formations is shown. The method 300 includes accessing the microorganisms 302 in a carbonaceous material containing geologic formation. Then an analysis of the microorganism formation environment may be conducted, which includes measuring the chemical composition that exists in the environment 304. This may include an in situ analysis of the chemical environment, and/or extracting gases, liquids, and solid substrates from the formation for a remote analysis.

For example, extracted formation samples may be analyzed using spectrophotometry, NMR, HPLC, gas chromatography, mass spectrometry, voltammetry, and other chemical instrumentation. The tests may be used to determine the presence and relative concentrations of elements like dissolved carbon, phosphorous, nitrogen, sulfur, magnesium, manganese, iron, calcium, zinc, tungsten, cobalt and molybdenum, among other elements. The analysis may also be used to measure quantities of polyatomic ions such as $PO_2^{3-}$, $PO_3^{3-}$, and $PO_4^{3-}$, $NH_4^+$, $NO_2^-$, $NO_3^-$, and $SO_4^{2-}$, among other ions. The quantities of vitamins, and other nutrients may also be determined. An analysis of the pH, salinity, oxidation potential (Eh), and other chemical characteristics of the formation environment may also be performed. Additional details of chemical analyses that may be performed are described in co-assigned PCT Application No. PCT/US2005/015259, filed May 3, 2005; and U.S. patent application Ser. No. 11/343,429, filed Jan. 30, 2006, of which the entire contents of both applications are herein incorporated by reference for all purposes.

A biological analysis of the microorganisms may also be conducted. This may include a quantitative analysis of the population size determined by direct cell counting techniques, including the use of microscopy, DNA quantification, phospholipid fatty acid analysis, quantitative PCR, protein analysis, etc. The identification of the genera and/or species of one or more members of the microorganism consortium by genetic analysis may also be conducted. For example, an analysis of the DNA of the microorganisms may be done where the DNA is optionally cloned into a vector and suitable host cell to amplify the amount of DNA to facilitate detection. In some embodiments, the detecting is of all or part of ribosomal DNA (rDNA), of one or more microorganisms. Alternatively, all or part of another DNA sequence unique to a microorganism may be detected. Detection may be by use of any appropriate means known to the skilled person. Non-limiting examples include restriction fragment length polymorphism (RFLP) or terminal restriction fragment length polymorphism (TRFLP); polymerase chain reaction (PCR); DNA-DNA hybridization, such as with a probe, Southern analysis, or the use of an array, microchip, bead based array, or the like; denaturing gradient gel electrophoresis (DGGE); or DNA sequencing, including sequencing of cDNA prepared from RNA as non-limiting examples. Additional details of the biological analysis of the microorganisms is described in co-assigned U.S. patent application Ser. No. 11/099,879, filed Apr. 5, 2005, the entire contents of which is herein incorporated by reference for all purposes.

The method 300 also includes providing an amendment to the microorganisms in the formation 306. Embodiments of the present invention include providing amendments of hydrogen, phosphorous compounds, and/or carboxylate compounds (e.g., acetate) to the microorganisms. The amendments may also include vitamins, minerals, metals, yeast extracts, and other nutrients. The amendments may still further include water amendments to dilute metabolic inhibitors and/or the microorganism consortium.

The effect of the amendments can be analyzed by measuring the concentration of a metabolic intermediary or metabolic product 308 in the formation environment. If the product concentration and/or rate of product generation does not appear to be reaching a desired level, adjustments may be made to the composition of the amendment 310. For example, if an acetate amendment does not appear to be activating the microorganisms after a set period of time (e.g., 90 days or more), a different amendment may be introduced to stimulate the microorganisms (e.g., hydrogen and/or phosphorous compounds).

The method 300 may also include removing the metabolic product 312 from the formation. Removal may be triggered when the concentration of the reaction product increases above a threshold level in the formation. In some of these instances, removal may performed to keep the product in a concentration range that has been found to stimulate the microorganisms to generate more of the product.

In additional embodiments, removal of the metabolic product may be done independently of the product concentration in the formation. For example, the reaction products may be continuously removed from the formation as part of a process that cycles the amendment through the formation. The mixture of metabolic products, amendment components and other materials removed from the formation may be processed to separate the products from components that will be sent back into the formation.

EXPERIMENTAL

Hydrogen and Phosphorus Compound Amendments

Experiments were conducted to compare biogenic methane generation from coal samples after introducing an amendment of hydrogen gas, a phosphorous compound, and ammonia. For each experiment, methane generation from coal samples from the Monarch coal seam in the Powder River Basin in Wyoming was periodically measured over the course of about 627 days. Each 5 gram coal sample was placed in a 30 ml serum bottle with 15 mL of water that was also taken from the formation. The coal and formation water were placed in the serum bottle while working in an anaerobic glove bag. The headspace in the bottle above the sample was flushed with a mixture of $N_2$ and $CO_2$ (95/5).

Amendments were then added to the samples. In a second set of experiments, 4.5 mL of $H_2$ gas (i.e., 179 µmol of $H_2$) was added to each bottle. Also added to the bottles was 0.15 mL of a 2500 mg/L (as N) aqueous ammonium chloride solution to provide a concentration of 25 mg/L, as nitrogen, to the samples, and 0.04 mL of a 1800 mg/L potassium phosphate solution that provided a concentration of 5 mg/L, as phosphate, to the samples. In a second set of experiments, the same amount of $H_2$ was added to the bottles, but no ammonium chloride or potassium phosphate. A third set of experiments introduced the ammonium chloride and potassium phosphate at the same levels as the first set, but no hydrogen gas was added. The samples were then sealed, removed from the glove box, and stored at room temperature over the course of the experiments.

The methane levels in the headspace above the samples was periodically measured and recorded. The methane was measured by running samples of the headspace gases through a gas chromatograph equipped with a thermal conductivity detector. The highest levels of methane production after 627 days occurred in samples treated with an amendment of hydrogen gas, ammonium chloride, and potassium phosphate, with average levels reaching 248 µmol of $CH_4$. This compares with 128 µmol $CH_4$ for samples just having the $H_2$ amendment, and 64 µmol $CH_4$ for samples just having the ammonia and phosphorous compound amendment.

The combination of the hydrogen and potassium phosphate generated more methane than can be accounted for by methanogenic conversion of the added hydrogen to methane. In the methanogenic metabolism of hydrogen to methane, four moles of molecular hydrogen and 1 mole of carbon dioxide are converted into 1 mole of methane:

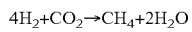

$$4H_2 + CO_2 \rightarrow CH_4 + 2H_2O$$

This means the 179 µmols of $H_2$ added to the sample bottles could, at most, be converted into 44.7 µmols of methane. For samples measuring peak methane production of 248 µmols, this leaves 203 µmols coming from other sources. Samples without hydrogen amendments produced about 63 µmols of methane from these coal substrates. This still leaves at least 185 µmols of methane that was generated from another source.

The source of the additional methane is believed to come from the biogenic metabolism of the coal into methane. The hydrogen and phosphorous compound amendment is believed to have stimulated the microorganisms present in the sample to metabolize the coal into methane. The stimulatory effect of the hydrogen and phosphorous amendment is not limited to enhancing the conversion of the added hydrogen gas to methane. It also includes stimulating the microorganisms to use methanogenic metabolic pathways that convert the coal substrate into methane.

Acetate Amendments

Experiments were conducted to measure the effects of acetate amendments on methane production from samples of carbonaceous materials. The carbonaceous materials used in these experiments were coal samples taken from underground coal beds at the Monarch coal site. The samples were transported under anaerobic conditions to 30 ml serum bottles, where 1 gram samples of the coal were combined in an anaerobic glove box with 20 mL of formation water from the same site and 0.2 mL of cell concentrate. The cell concentrate consisted of cells from about 6.6 L of formation water added to 15 mL of formation water. The headspace in the bottle above the sample was exchanged with a mixture of $N_2$ and $CO_2$ (95/5).

Figure 5:
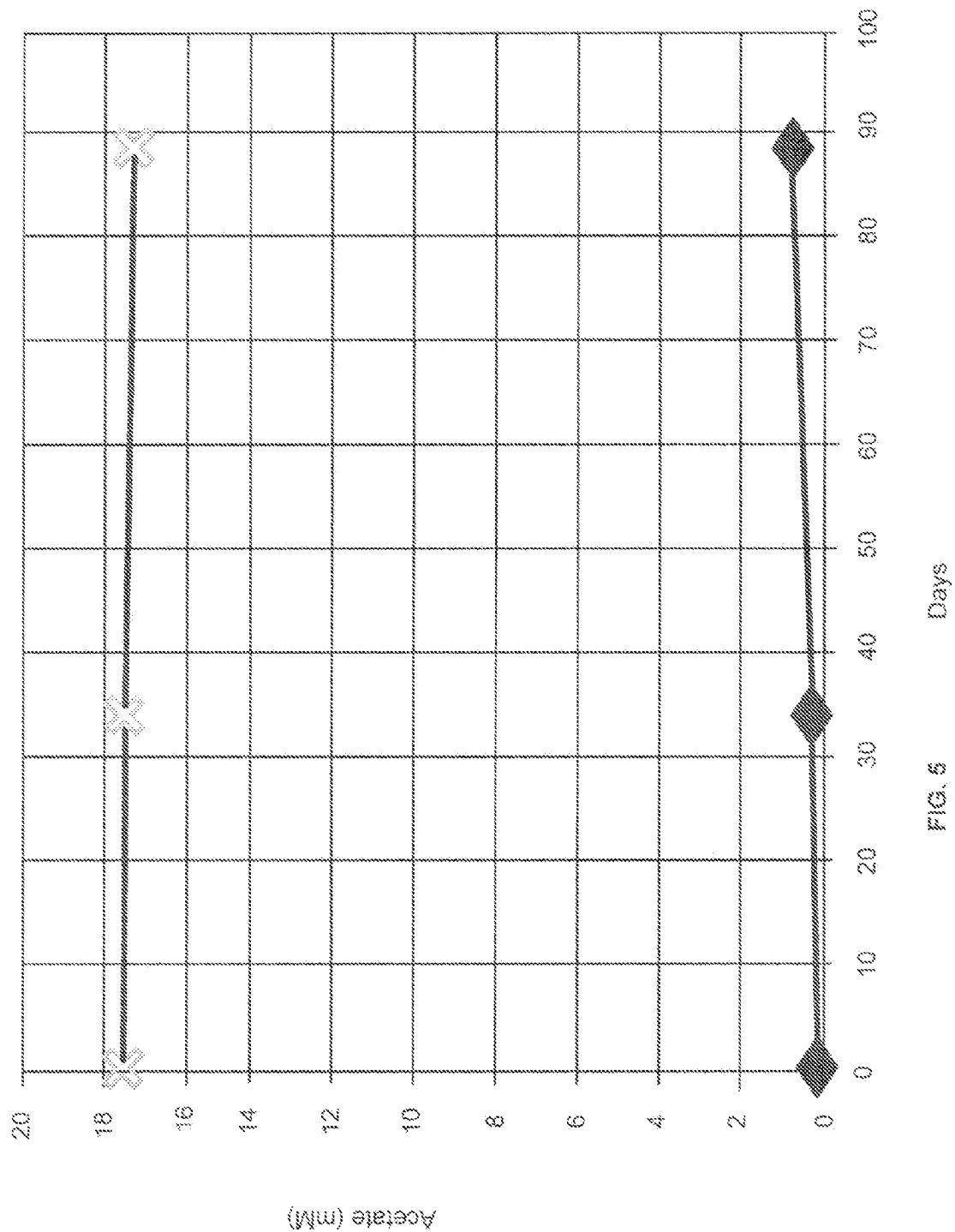
FIG. 5 is a plot showing acetate concentration over time in samples where an acetate amendment has been introduced.

In a first set of samples, the acetate amendment included adding an aqueous sodium acetate solution to the sample bottles to give the samples a 10 mg/mL acetate concentration. A second set of control samples were prepared in the same manner except for lacking the acetate amendment. Methane levels (measured as a mol. % methane in the headspace of the sample bottle) were periodically measured in both the amendment and control samples over the course of 90 days. FIG. 5 shows a plot of the methane levels measured in these samples as a function of time.

Figure 4:
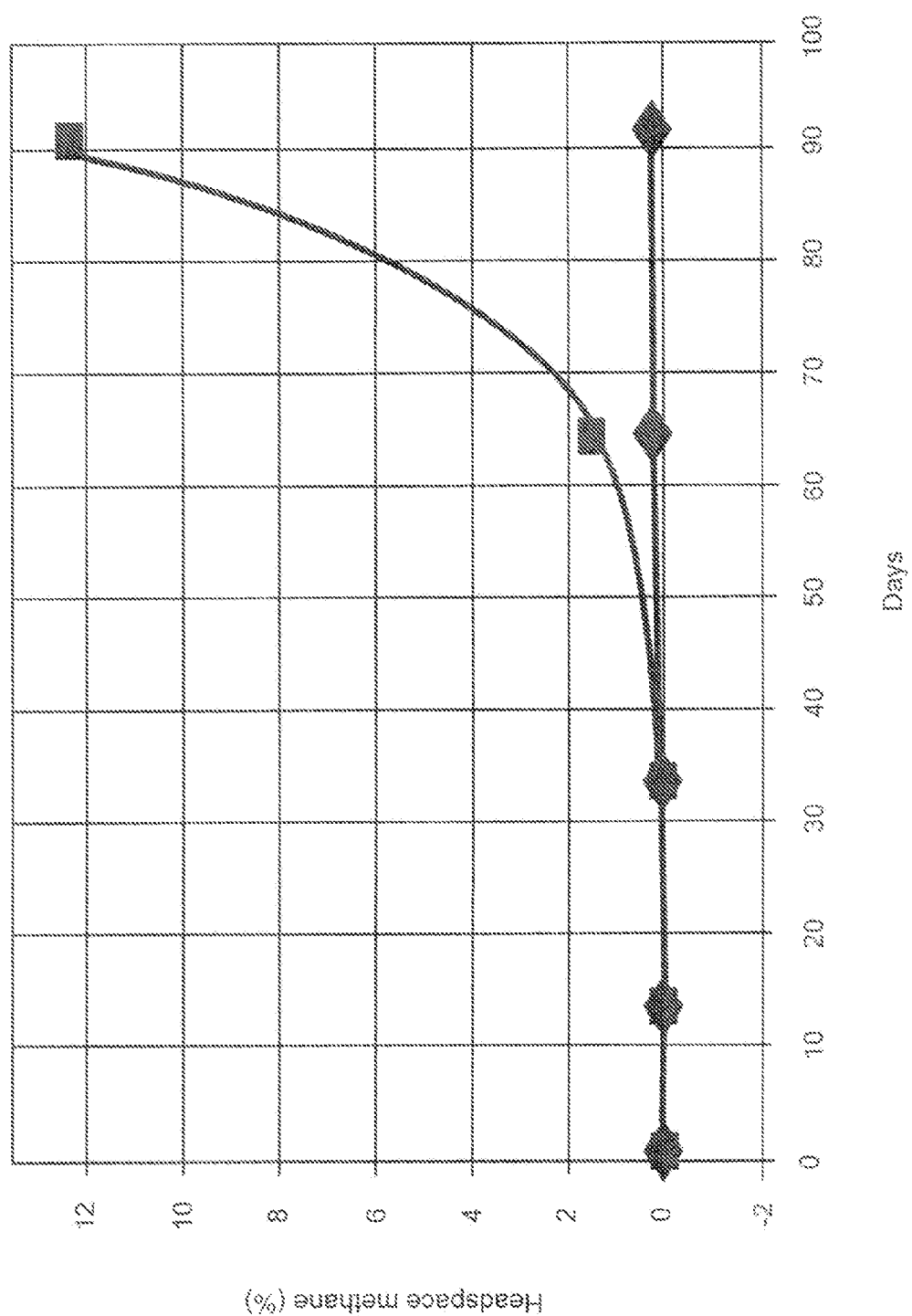
FIG. 4 is a plot that compares methane concentrations in an unamended sample with a sample treated with an acetate amendment.

As FIG. 4 reveals, very little methane generation occurred in either the amendment or control sample during the first 50 days. But the measurement taken on day 65 shows the methane levels starting to build in the acetate amendment sample while the control sample continued to show negligible methane generation. By the 90th day, the acetate amendment sample showed rapid and significant methane generation with methane representing over 12 mol. % of the headspace in the sample bottles. Meanwhile, the control samples that lacked the acetate amendment still showed almost no methane generation after 90 days.

Plot of FIG. 4 clearly shows that the acetate amendment had a significant impact on methane generation after an activation period of about 65 days. But the plot did not show whether the methane was produced by the methanogenic conversion of the acetate into methane, or whether the methane was derived from the coal sample. Thus, a second measurement was made of the acetate concentration in the samples over the same period of time.

FIG. 5 shows the plot of the acetate concentrations over time in the samples. The plot reveals that the acetate concentration did not change significantly over the 90 day period. Most significantly, little change in the acetate concentration was observed before and after the methane generation rapidly increased in the acetate amendment samples. These data indicate that the acetate amendment acted as an activation agent to enhance the methanogenic metabolism of the coal into methane. The data also show that the acetate activation does not occur immediately, and that a delay of several weeks to months may occur before the start of significant methanogenic activity.

Phosphorous Compound Amendments and Rollover

Rollover is a condition where the rate of biogenic methane production starts to plateau as the in situ methane concentration reaches a certain level. In many instances, the rate flattens to zero, and the methane concentration remains constant over time. The rollover point (i.e., the point where the methane concentration begins to break from a monotonically increasing state) can vary between microorganism consortia, but appears to be reached in almost all unamended samples of carbonaceous material that have been examined to date.

Figure 6:
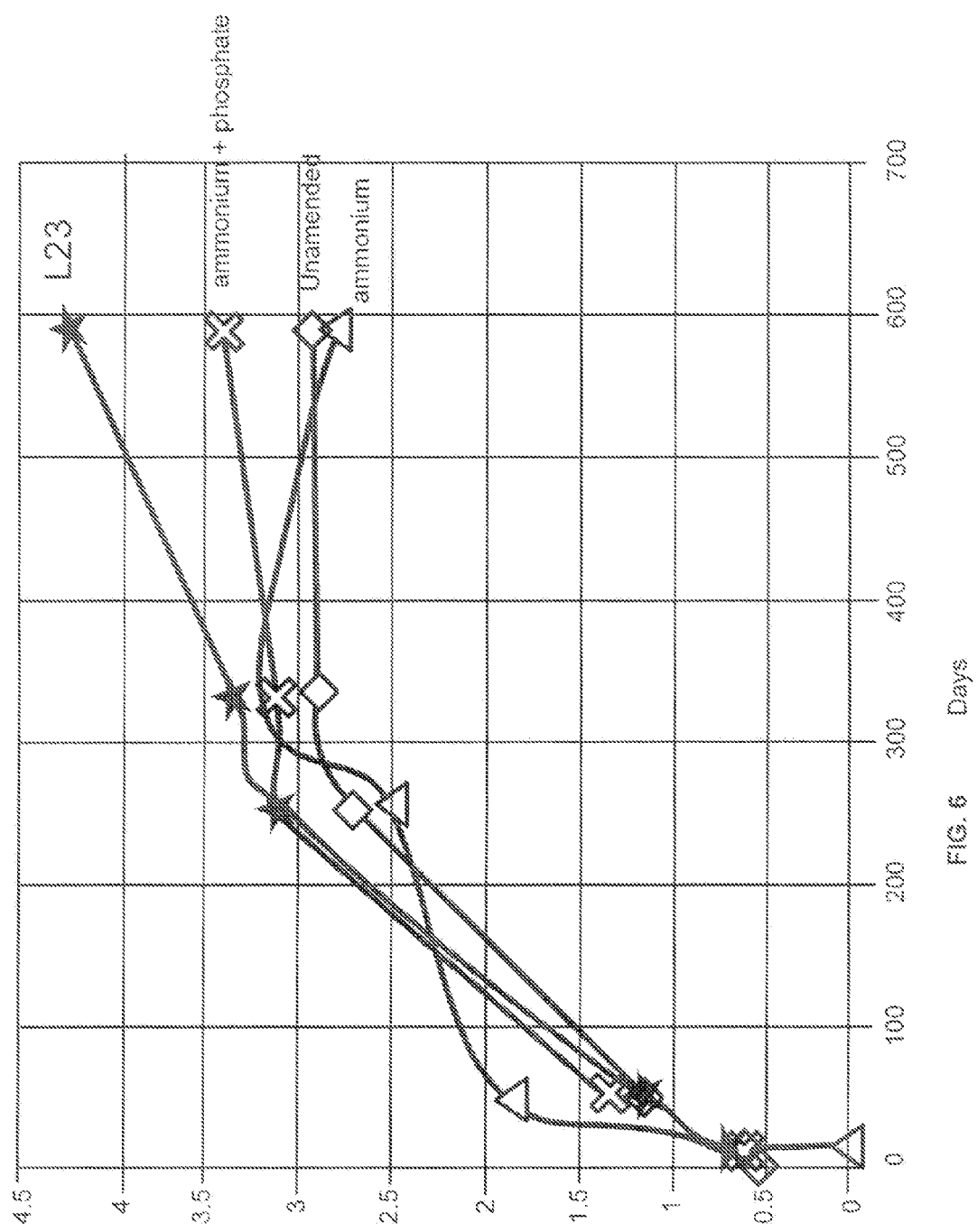
FIG. 6 is a plot of methane concentration over time in an unamended sample, and samples amended with a phosphorous compound or ammonia.

But some samples receiving minerals, metals and nutrient amendments exhibited less of a rollover effect than unamended controls. Further tests revealed that the agents responsible for reducing rollover were phosphate compounds, such as sodium or potassium phosphate. FIG. 6 shows a plot of methane levels over time in the headspace of 30 ml serum bottles containing amended and unamended coal samples. The plot for the unamended sample shows the rollover point occurring when the methane level in the headspace reaches between 2.5 and 3 mol. %. At these methane levels, the rate of methane production starts to decrease and the methane level remains constant at slightly under 3 mol. %.

A more volatile, but similar pattern was observed for samples treated with an ammonium amendment. In these samples, ammonium chloride was introduced to give each sample a concentration of 25 mg/L nitrogen at the start of the methane measurements. The rate of methane production in these samples was initially greater than for the unamended samples or samples with other types of amendments (including an amendment of ammonium and phosphate). In addition, the peak methane level in the ammonium samples exceeded the peak plateau levels in the unamended samples. But eventually the methane levels began to decrease, and by about day 600 the methane levels in the samples were about the same as those measured in the unamended samples.

The samples treated with an amendment that included a phosphorous compound (i.e., potassium phosphate) all appeared to breakthrough the plateau methane level observed in the samples that were prone to rollover. As FIG. 6 shows, samples treated with a pure 5 mg/L potassium phosphate amendment had a methane level of about 4.3 mol. % after 600 days, or about 43% higher than samples without phosphate. Amendments with ammonium chloride and phosphate did not result in substantial increases.

Figure 7:
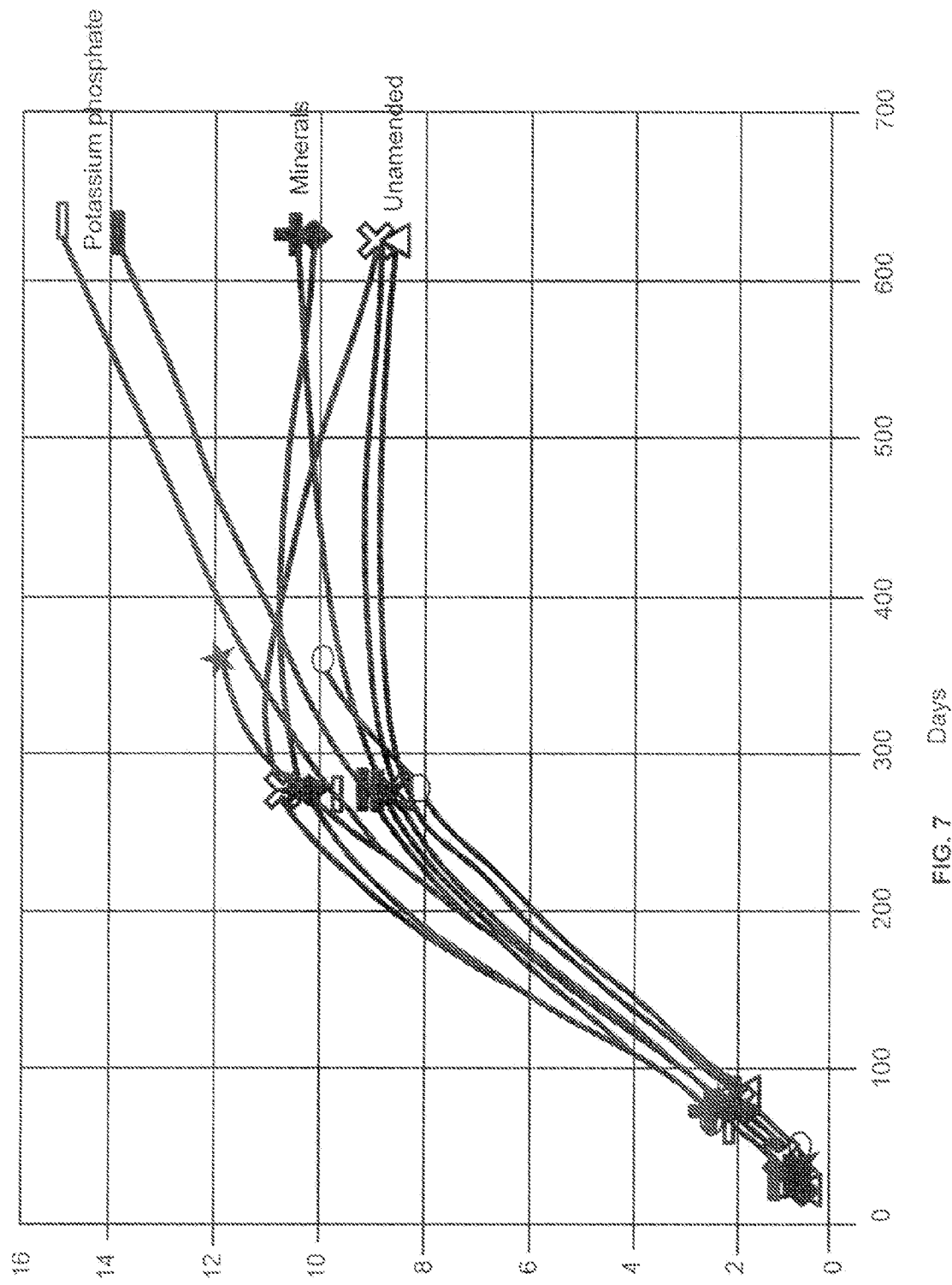
FIG. 7 is a plot of methane concentration over time in an unamended sample, and samples amended with a phosphorous compound or a mineral composition.

FIG. 7 shows another plot of methane concentration over time for samples with and without phosphorous compound amendments. Similar to the plot in FIG. 7, this plot shows samples that were not treated with a phosphorous amendment (i.e., a potassium phosphate amendment) reached a rollover point beyond which the methane concentration did not increase. In contrast, no plateau was observed in the methane concentration of two sets of samples that were treated with a phosphate amendment. At the end of just over 600 days, the phosphate containing samples had significantly higher methane levels than samples treated with a minerals amendment or the samples that were unamended.

FIGS. 6 and 7 indicate that phosphorous compounds such as potassium phosphate can extend methanogenesis supported by complex hydrocarbons. Thus, the introduction of a phosphorous compound amendment to microorganisms in a geologic formation may stimulate the microorganisms to continue to produce methane in an environment where they are already exposed to high levels of methane.

Having described several embodiments, it will be recognized by those of skill in the art that various modifications, alternative constructions, and equivalents may be used without departing from the spirit of the invention. Additionally, a number of well known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the microorganism" includes reference to one or more microorganisms and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A method of stimulating biogenic production of methane, the method comprising:
   accessing a consortium of microorganisms in an anaerobic geologic formation that includes a naturally formed in situ carbonaceous material;
   providing an $H_2$ gas injection to the microorganisms; and
   providing a phosphorous compound to the microorganism, wherein the combination of the $H_2$ and phosphorous compound stimulates the consortium to metabolize the carbonaceous material into the methane.

2. The method of claim 1, wherein the phosphorous compound comprises a phosphate compound.

3. The method of claim 2, wherein the phosphate compound comprises a phosphate salt.

4. The method of claim 3, wherein the phosphate compound is selected from the group consisting of sodium phosphate and potassium phosphate.

5. The method of claim 1, wherein the phosphorous compound comprises a phosphorous oxyacid or a salt of a phosphorous oxyacid.

6. The method of claim 5, wherein the phosphorous oxyacid comprises $H_3PO_4$, $H_3PO_3$, or $H_3PO_2$.

7. The method of claim 5, wherein the salt of the phosphorous oxyacid comprises dibasic sodium phosphate or dibasic potassium phosphate.

8. The method of claim 1, wherein the method further comprises providing a yeast extract to the microorganisms.

9. The method of claim 1, wherein the carbonaceous material comprises coal, oil, carbonaceous shale, oil shale, tar sands, tar, lignite, kerogen, bitumen, or peat.

10. The method of claim 1, wherein the metabolism of the carbonaceous material to the metabolic product comprises one or more intermediate metabolic steps that produce one or more intermediate metabolites.

11. The method of claim 10, wherein the one or more intermediate metabolites comprise a compound selected from the group consisting of organic acids, alcohols, amines, straight or branched alkyl hydrocarbons, and aromatic hydrocarbons.

12. The method of claim 11, wherein the one or more intermediate metabolites is metabolized into the metabolic product with enhanced hydrogen content.

13. The method of claim 1, wherein the method further comprises providing a vitamin amendment to the microorganisms.

14. The method of claim 1, wherein the method further comprises providing a trace metal amendment to the microorganisms.

15. The method of claim 1, wherein the method further comprises providing a mineral amendment to the microorganisms.

16. A method of stimulating biogenic production of methane, the method comprising:
accessing microorganisms in an anaerobic geologic formation that includes a naturally formed in situ carbonaceous material;
injecting molecular hydrogen to the geologic; and
providing a phosphorous compound to the geologic formation,
wherein the combination of the molecular hydrogen and the phosphorous compound stimulates the microorganisms to metabolize the carbonaceous material into the methane.

17. The method of claim 16, wherein the combination of the molecular hydrogen and the phosphorous compound is an activation agent for the microorganisms to metabolize the carbonaceous material in the geologic formation into methane.

18. A method of stimulating biogenic production of a metabolic product with enhanced hydrogen content, the method comprising:
accessing microorganisms in an anaerobic geologic formation that includes carbonaceous material;
detecting a plateau in a concentration of the metabolic product with enhanced hydrogen from the first geologic formation that is indicative of a rollover effect;
providing molecular hydrogen and a phosphorous compound to the geologic formation,
wherein the molecular hydrogen and the phosphorous compound increase the concentration of the metabolic product with enhanced hydrogen content to a level greater than a rollover point where the rollover effect began to occur.

19. The method of claim 18, wherein the concentration of the metabolic product reaches a local maxima due to the rollover effect and the molecular hydrogen and the phosphorous compound increases the concentration above a level of the local maxima.

20. The method of claim 18, wherein the combination of the molecular hydrogen and the phosphorous compound is an activation agent for the microorganisms to metabolize the carbonaceous material in the geologic formation into methane.

* * * * *